(12) United States Patent
Lau et al.

(10) Patent No.: US 11,268,059 B2
(45) Date of Patent: Mar. 8, 2022

(54) APPARATUSES, SYSTEMS, AND METHODS FOR CULTURING CELLS

(71) Applicant: eXo Cell, LLC, New Orleans, LA (US)

(72) Inventors: Frank Ho Pak Lau, New Orleans, LA (US); Steven Douglas Scahill, New Orleans, LA (US)

(73) Assignee: EXO CELL, LLC, New Orleans, LA (US)

( * ) Notice: Subject to any disclaimer, the term of this patent is extended or adjusted under 35 U.S.C. 154(b) by 0 days.

(21) Appl. No.: 16/456,941

(22) Filed: Jun. 28, 2019

(65) Prior Publication Data

US 2019/0382705 A1    Dec. 19, 2019

Related U.S. Application Data

(62) Division of application No. 15/292,759, filed on Oct. 13, 2016, now Pat. No. 10,344,256.

(60) Provisional application No. 62/240,612, filed on Oct. 13, 2015.

(51) Int. Cl.

| | |
|---|---|
| *C12M 1/12* | (2006.01) |
| *C12N 5/0775* | (2010.01) |
| *C12M 3/00* | (2006.01) |
| *C12M 1/22* | (2006.01) |
| *C12N 5/077* | (2010.01) |
| *G01N 33/50* | (2006.01) |

(52) U.S. Cl.
CPC ............ *C12M 25/06* (2013.01); *C12M 21/08* (2013.01); *C12M 23/10* (2013.01); *C12N 5/0653* (2013.01); *C12N 5/0662* (2013.01); *G01N 33/5044* (2013.01); *C12N 2513/00* (2013.01)

(58) Field of Classification Search
CPC ...... C12M 25/06; C12M 21/08; C12M 23/10; C12N 5/0653; C12N 5/0662; C12N 2513/00; G01N 33/5044
USPC ........................................................ 435/366
See application file for complete search history.

(56) References Cited

FOREIGN PATENT DOCUMENTS

EP     1 690 928 A1    8/2006

OTHER PUBLICATIONS

Loskill et al., Organs-on-a-chip—Microphysiological platforms as in vitro models of cardiac and adipose tissue, European Biophysics Journal, 44 (Suppl 1), (Published Jun. 26, 2015), p. 529.*
Bartelt et al., Adipose tissue browning and metabolic health, Nature Reviews Endocrinology, vol. 10 (Published Oct. 22, 2013), pp. 24-36.*
Mai et al., An Evolving New Paradigm: Endothelial Cells—Conditional Innate Immune Cells, Journal of Hematology & Oncology, 2013, vol. 6, No. 61, pp. 1-13.
PCT International Search Report for International Application No. PCT/US2016/056879, dated Nov. 28, 2016, 5 pages.
Written Opinion of the International Searching Authority for International Application No. PCT/US2016/056879, dated Nov. 28, 2016, 7 pages.
Sasagawa et al., Endothelial Colony-Forming Cells for Preparing Prevascular Three-Dimensional Cell-Dense Tissues Using Cell-Sheet Engineering, Journal of Tissue Engineering and Regenerative Medicine, 2016, vol. 10, pp. 739-747.
Sorrell et al., The Creation of an in vitro Adipose Tissue that Contains a Vascular-Adipocyte Complex, Biomaterials, 2011, vol. 32, pp. 9667-9676.
Ballester-Beltran et al., Dorsal and Venlral Stimuli in Cell-Material Interactions: Effect on Cell Morphology, Biointerphases, 2012, vol. 7, No. 39, 10 pages.
Non-Final Office Action issued in U.S. Appl. No. 15/292,759, dated Apr. 10, 2018, 9 pages.
Final Office Action issued in U.S. Appl. No. 15/292,759, dated Nov. 23, 2018, 11 pages.
Loskill et al., Lab Chip. May 2, 2017; 17(9):1645-1654 (Author manuscript available in PubMed Central on May 2, 2018).

* cited by examiner

*Primary Examiner* — Jennifer M. H. Tichy
(74) *Attorney, Agent, or Firm* — Ascenda Law Group, PC

(57) ABSTRACT

Apparatuses, systems, and methods are provided for culturing a buoyant target tissue. Embodiments include a first surface configured to culture a first layer of supporting cells, and a second surface configured to culture a second layer of supporting cells. The first layer of supporting cells may be formed on a portion of the first surface and the second layer of supporting cells may be formed on a portion of the second surface. The buoyant target tissue may be added to the first layer of supporting cells. The second layer of supporting cells may be placed on the first layer of supporting cells such that the buoyant target tissue is sandwiched between the first layer of supporting cells and second layer of supporting cells.

15 Claims, 14 Drawing Sheets
(12 of 14 Drawing Sheet(s) Filed in Color)

Differentiated "adipocytes"    Primary adipocytes

FIG. 9A
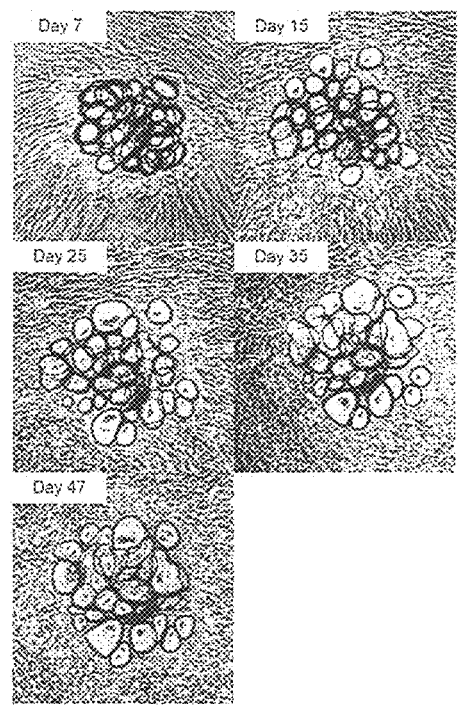
FIG. 9B
FIG. 9

APPARATUSES, SYSTEMS, AND METHODS FOR CULTURING CELLS

This application claims the benefit of U.S. Provisional Patent Application No. 62/240,612, filed Oct. 13, 2015, which is incorporated herein by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 9 shows microscopic images illustrating the morphologic stability of a sandwiched White Adipose Tissue (SWAT) cell culture system, according to an exemplary embodiment of the present disclosure.

FIG. 9A shows microscopic images of a SWAT culture system having a bi-layer of supporting cells surrounding a WAT cell cluster, according to an exemplary embodiment of the present disclosure.

FIG. 9B shows microscopic images illustrating the morphologic stability of WAT cell clusters in the SWAT cell culture system, according to an exemplary embodiment of the present disclosure.

DESCRIPTION OF EMBODIMENTS

Obesity is an increasingly common condition afflicting over 79 million Americans. Obesity may be associated with various diseases including: type 2 diabetes, heart disease, stroke, arthritis, and some cancers. In addition to the health impact, the direct financial cost related to treatment of obesity and related diseases is estimated to exceed $150 billion in the United States alone. Presently, there is a strong need for anti-obesity therapeutics approved for human intervention.

Obesity may be described as an overgrowth of white adipose tissue (WAT) in the body. In general, WAT may be considered an organ in the human body, functioning as an energy reservoir where extra calories may be stored. WAT is found throughout the human body and may be subcutaneous in origin, or originate from a variety of anatomical areas including, intra alia, the abdomen, chest, gluteus, and limbs. WAT may also be considered an endocrine organ that produces hormones to regulate multiple physiological systems, e.g., hunger/satiety, glucose metabolism, and lipid metabolism. A properly functioning WAT organ is critical. Indeed, insufficient WAT may lead to illness or death.

As an organ, WAT includes mature, adipocytes (wAds) that may be described morphologically as large cells having a unilocular lipid droplet that exceeds 95% of cellular volume. The presence of this large lipid droplet renders wAds buoyant. Human wAds may also be considered as exceptionally fragile cells due in large part to their size. For example, human wAds range in size from about 100 to about 140 μm in size, which is nine (9) times the volume of rodent wAds.

Attempts to culture primary, human wAds have largely been unsuccessful. Conventional in vitro culture methodologies employ techniques such as enzymatic treatment and and mechanical handling to dissociate primary WAT tissue and isolate wAds. This treatment typically destroys or severely damages a large proportion of the wAds, wherein the majority of wAds undergo cell lysis within 72 hours after handling. Accordingly, research models of human WAT derived from wAds do not exist.

Figure 1A:
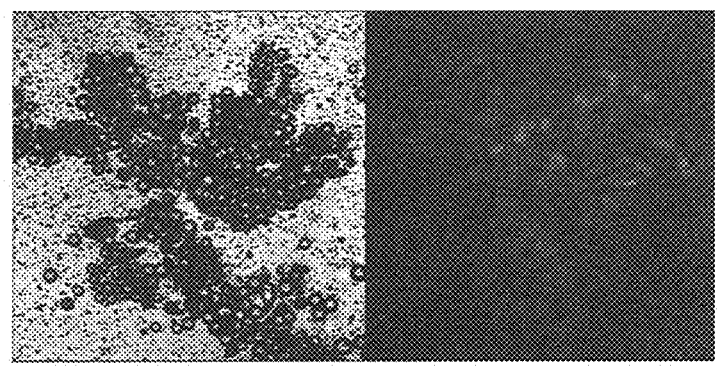
FIG. 1A shows microscopic images of human white adipose tissue (WAT) cultured in a matrix of collagen after 2 days of conventional, collagen-embedded culture.
Figure 1B:
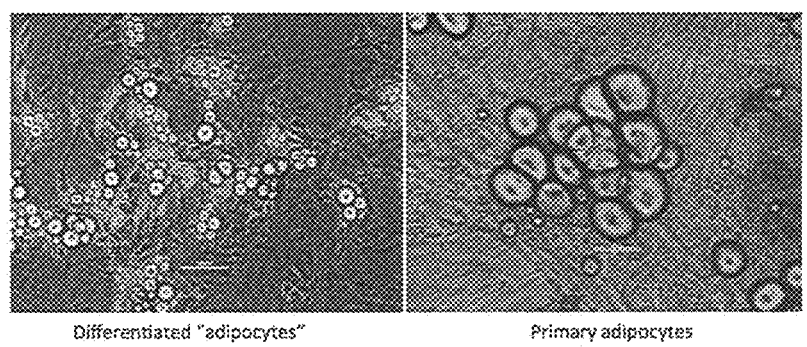
FIG. 1B shows microscopic images illustrating differences in morphology between differentiated "adipocytes" (diffAds) and primary adipocytes.

Attempts to overcome the challenge associated with wAds culture include embedding wAds in a matrix of collagen protein. However, this technique has had limited success. FIG. 1 shows micrographs of collagen-embedded human WAT stained with propidium iodine indicating the induction of programmed cellular death, a.k.a., apoptosis, after 2 days of culture. In addition to their fragility, adipocytes are also considered terminally differentiated and mitotically inactive. Therefore, wAds may not be expanded in culture without altering their differentiation state, i.e., dedifferentiating.

Unlike most other model cell types, for which stocks of cells may be frozen for long-term storage, human WAT/wAds must be obtained fresh from the operating room or clinic and used immediately for each experiment. Researchers must, therefore, rely on surgically procured, human WAT tissue as a source material, which limits the availability of WAT/wAds to non-clinician researchers. In fact, researchers lacking relationships with clinicians may not have access to human WAT. Research experiments may then become tied to clinician schedules, which can be unpredictable. Further, tissue procurement may be time-consuming, and often requires travel, donning of surgical attire, and hospital approval of investigational protocols. These barriers to accessing source WAT have slowed the overall pace of scientific discovery and may deter researchers from investigating the biology of human WAT altogether.

Currently, researchers rely on models including rodent models or stromal/stem cell models chemically differentiated into adipocytes (i.e., diffAds). However, these experimental models fail to recapitulate primary, human WAT biology. For example, one of the first-identified anti-obesity pathways was controlled by beta-3 adrenoreceptors (ß3-ARs). Using selective ß3-AR agonists, obesity and diabetes were successfully cured in several rodent models. However, the same selective ß3-AR that were successful in rodent models of obesity had little activity against human ß3-ARs, resulting in multiple failed clinical trials.

Similarly, certain model cell types, e.g., stromal and stem cells, may be chemically differentiated into adipocytes (diffAds). However, diffAds only express human, wAds markers, including CCAAT/enhancer-binding protein alpha, lipoprotein lipase, fatty acid binding protein 4, and hormone sensitive lipase, at a reduced levels. Further, models of obesity based on diffAds fail to recapitulate wAds functionality in metabolic assays measuring glycerol release, adiponectin release, and glucose uptake.

Figure 2:
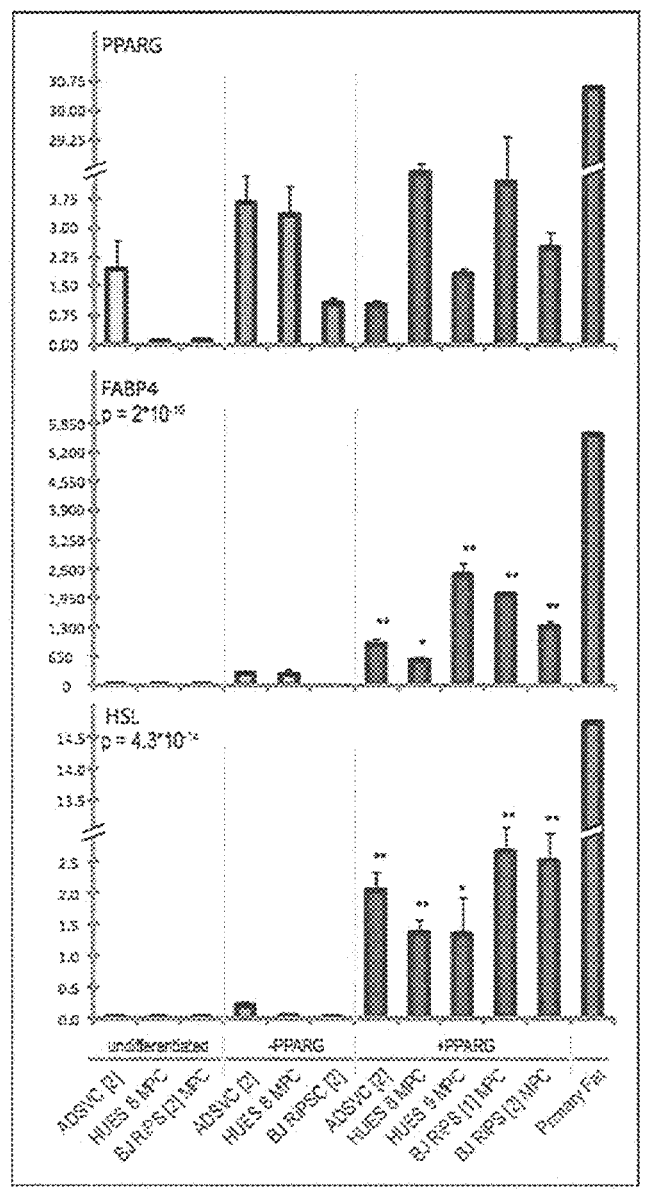
FIG. 2 is a graphical illustration comparing gene expression of adipocyte identity genes between conventional culture models and primary WAT.

Genetically, in vitro cell models do not share similar gene expression patterns with wAds. FIG. 2 graphically illustrates the variation in adipocyte identity gene expression between conventional culture models and primary WAT. The Green bars within FIG. 2 represent the expression levels of stem cells differentiated into multiloculated "adipocytes" (diffAds) using standard protocols. The Red bars within FIG. 2 represent the expression levels of stem cells differentiated into "adipocytes" using PPARg-expressing lentivirus constructs. The Blue bars within FIG. 2 represent the expression levels of primary adipose tissue. As shown, primary adipose tissue expresses adipocyte genes at levels 10 to 100 times greater than in vitro models. Accordingly, conventional models fail to recapitulate the gene expression levels of primary adipose tissues.

Apparatuses, methods and systems are provided for culturing tissues and cells. In exemplary, non-limiting embodiments, apparatuses, methods and systems are provided for culturing buoyant, primary, human tissue explants and cells under conditions capable of maintaining primary cell type characteristics, including morphology, gene and protein expression levels, and metabolic function, even after extended periods of time in culture.

In exemplary embodiments, apparatuses, methods, and systems for in vitro culture of buoyant tissue explants of human WAT are provided.

Embodiments of the present disclosure provide systems, methods, and apparatuses for culturing buoyant tissues and cells when added to an aqueous culture medium. Embodiments of the present disclosure provide systems, methods, and apparatuses for culturing primary, human tissue explants and cells obtained from individuals, e.g., patients. Embodiments of the present disclosure provide systems, methods, and apparatuses for culturing human tissue and cells for extended periods of time, e.g., several weeks, in a stable, undifferentiated state.

Embodiments of the present disclosure provide systems, methods, and apparatuses for configuring a micro-physiological, e.g., organ-on-a-chip, model system. Embodiments of the present disclosure provide for the evaluation of the effect of chemical compounds, such as pharmaceuticals, on human tissue explants and cells cultured via the systems, methods, and apparatuses disclosed herein.

Generally, in vitro tissue and cell culture systems employ culture vessels, e.g., dishes, plates, flasks, slides, to which tissues or cells are added along with a nutrient rich medium. In certain instances, culture dishes may provide a substrate to which tissues or cells may adhere, and the medium may provide the necessary components to support and promote metabolic function of the tissues and cells added thereto. Establishing a new culture of tissue or cells requires transferring sample tissues or cells to a culture dish having an aqueous culture medium. Tissue and cell types that are not buoyant may come to rest on the surface of a culture vessel where tissue or cellular attachment to the surface occurs through a complex process commonly referred to as cellular adhesion. However, certain tissue and cell types are buoyant, and therefore, float in their culture medium rather than adhere to the surface of a culture dish. For certain cell types, failure to adhere may result in cell death.

Embodiments of the present disclosure provide systems, methods, and apparatuses for in vitro culture of buoyant tissues and cells. In particular embodiments, the systems, methods, and apparatuses described herein may be adapted to culture all tissue and cell types including but not limited to: white adipose tissue (WAT), brown adipose tissue (BAT), brain, nervous system tissue, thyroid, pancreas, spleen, cartilage, liver, kidney, and bone.

Figure 3:
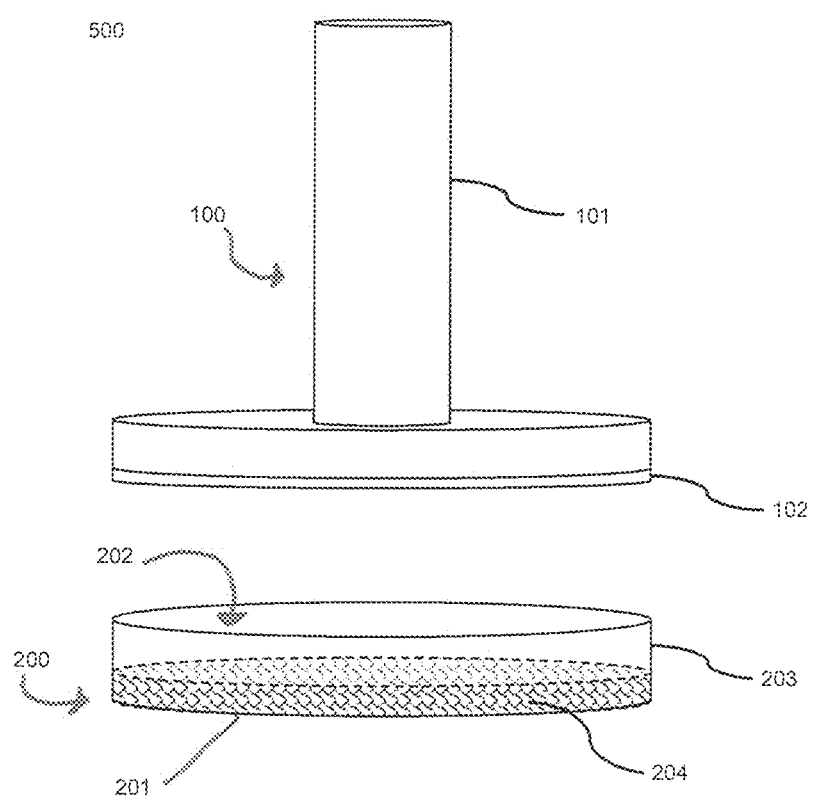
FIG. 3 is an isometric view of a culture apparatus having a layer of supporting cells disposed in a thermoresponsive dish and an insert device for removing the layer of supporting cells from the dish, according to an exemplary embodiment of the present disclosure.
Figure 4:
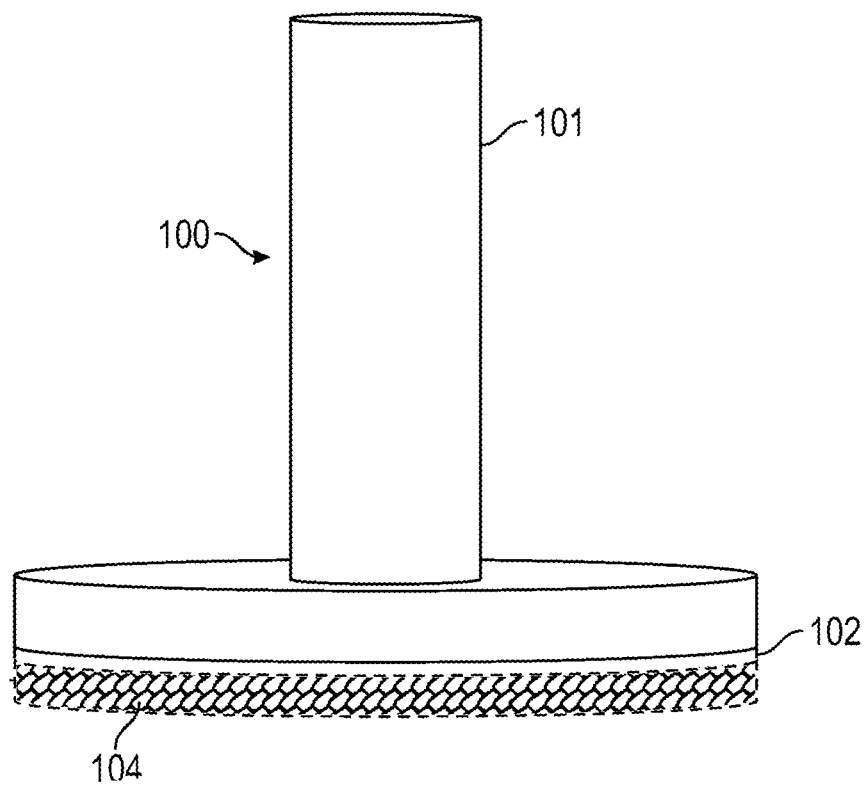
FIG. 4 is an isometric view of the insert device shown in FIG. 3 with the layer of supporting cells attached to a base of the insert device.

Referring to FIGS. 3 to 8, different views of a system for culturing buoyant cell types is shown. FIG. 3 illustrates an exemplary embodiment of a culture apparatus 500 for culturing buoyant cell types. Culture apparatus 500 may include a culture vessel 200, e.g., a culture dish 200, and an insert 100. In certain non-limiting embodiments, the culture vessel 200 and insert 100 may comprise materials that promote adhesion of tissues or cells to the surface of the vessel or the insert.

In some embodiments, adhesion-promoting materials may be a component of the vessel 200 or insert 100, per se. In other embodiments, adhesion-promoting materials may be added to the vessel 200 and/or insert 100. In this embodiment, the respective base/surface of the vessel 200 and/or insert 100 may be coated with a matrix of proteins or extracellular material. Non-limiting examples of adhesion promoting materials include but are not limited to poly(N-isopropylacrylamide) (pNIPAAM/pNIPAm), modified methylcellulose, and thermoresponsive materials, e.g., thermoresponsive polyelectrolyte multilayer films, gelatin, collagen, hyaluronic acid, and cellulose.

In an exemplary embodiment of the present disclosure, a culture vessel 200 may include a culture dish 200 having a base 201, side walls 203, and an opening 202. Base 201 of culture dish 200 may be configured to allow culture of at least one layer of supporting cells 204. Culture dish 200 may be configured to include an opening 202 for insertion of an insert 100 device.

As shown in FIG. 3, insert 100 may include a base 102 and a handle 101. Handle 101 may be configured to allow insertion through the culture dish opening 202. Base 102 may be configured to allow culture of at least one layer of supporting cells 104.

In various embodiments, a thermoresponsive layer may be added to the surface of a culture dish base 201 prior to culturing supporting cells. A layer of supporting cells 204 may be cultured on the surface of the thermoresponsive layer covering a culture dish base 201 or an insert surface 102. See, FIG. 3. Treatment of the culture dish 200 and the insert 100 surfaces with a thermoresponsive layer may allow transfer of an intact layer of supporting cells from either a culture dish 200 or the insert 100 to another culture dish or insert. See, FIG. 3, FIG. 4 and FIG. 5.

Figure 5:
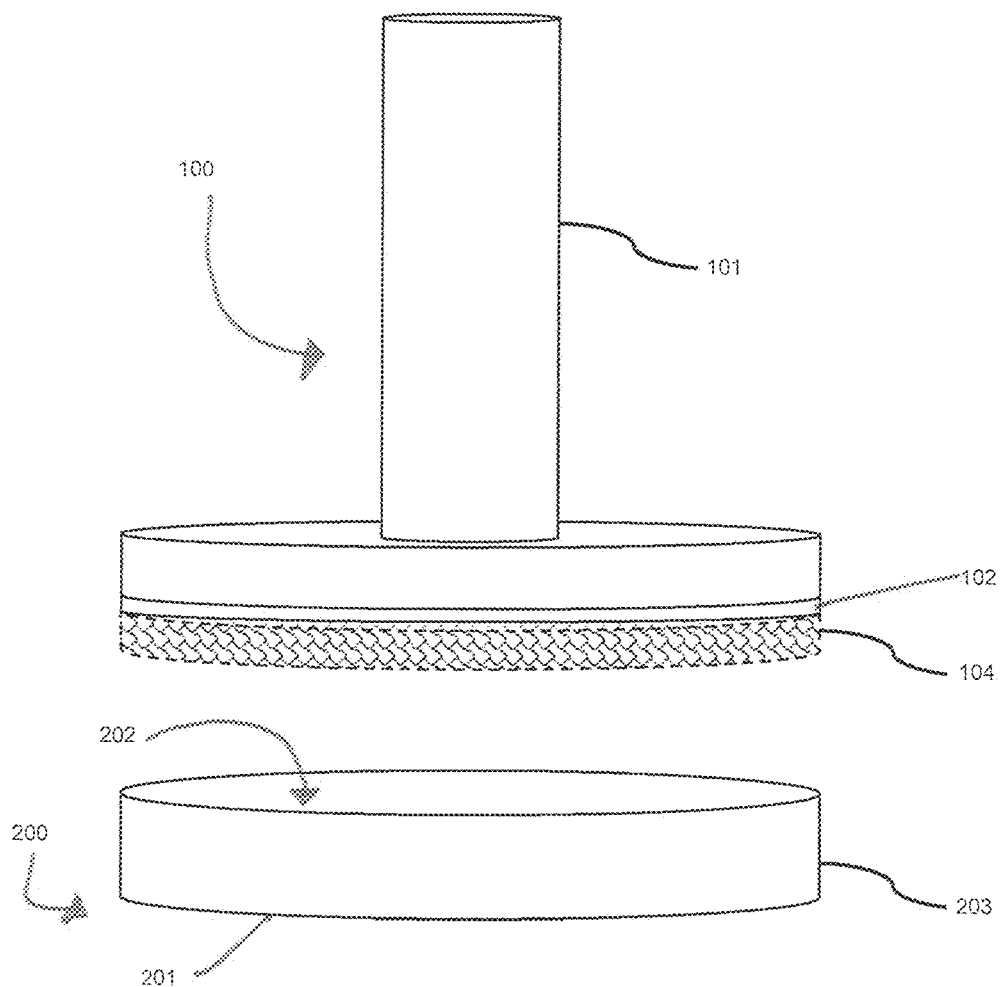
FIG. 5 is an isometric view of the culture apparatus shown in FIG. 4, with the layer of supporting cells attached to the base of the insert device being removed from the thermoresponsive dish.
Figure 6:
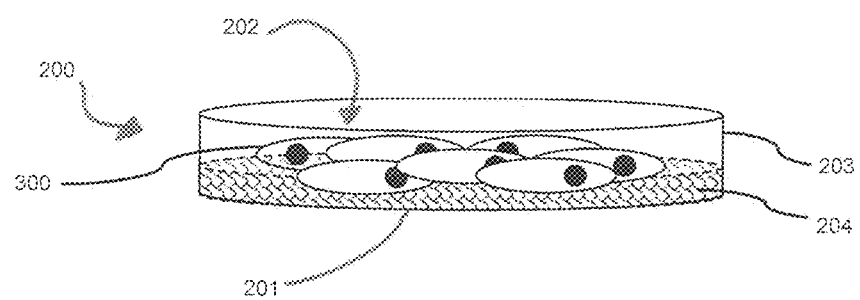
FIG. 6 is an isometric view of a culture apparatus having a buoyant cell or tissue explant deposited on a first layer of supporting cells in a thermoresponsive dish, according to an exemplary embodiment of the present disclosure.
Figure 7:
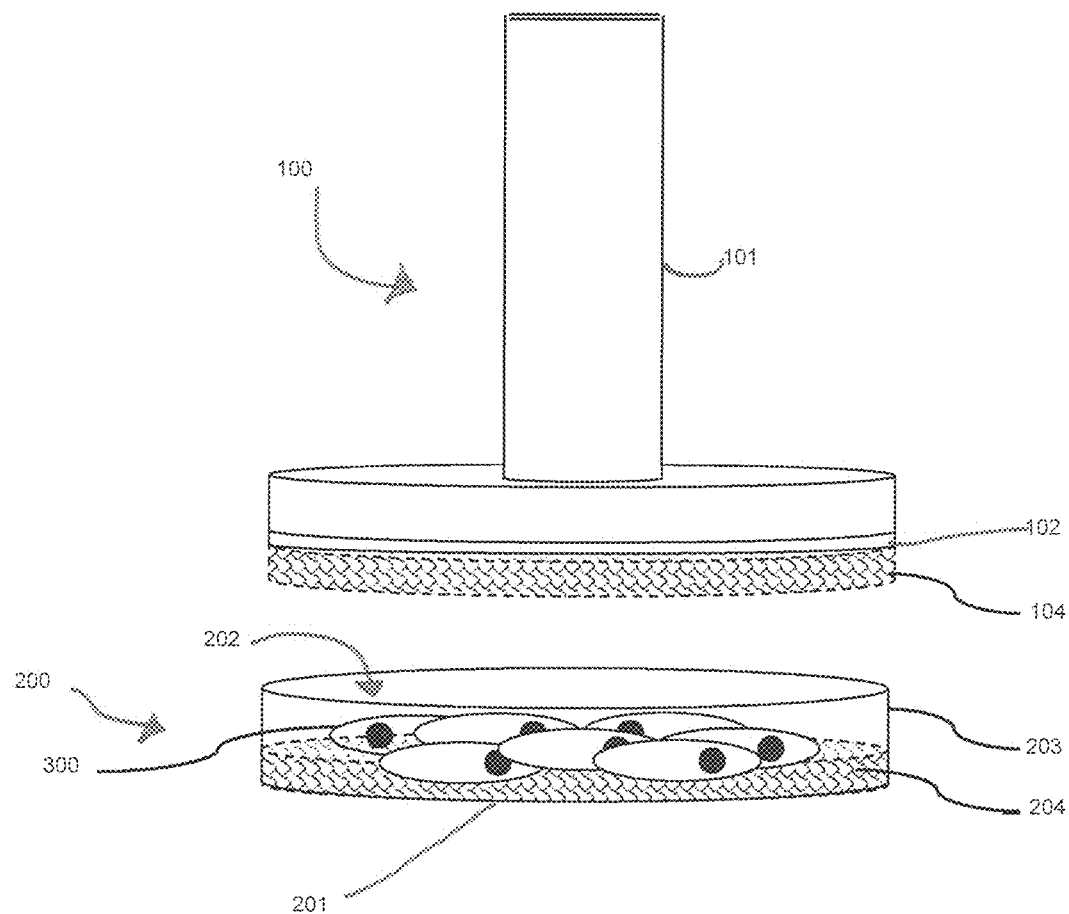
FIG. 7 is an isometric view of the culture apparatus shown in FIG. 6 and an insert device with a second layer of supporting cells attached to a base of the insert device to be deposited on top of the tissue explant and first layer of supporting cells, according to an exemplary embodiment of the present disclosure.
Figure 8:
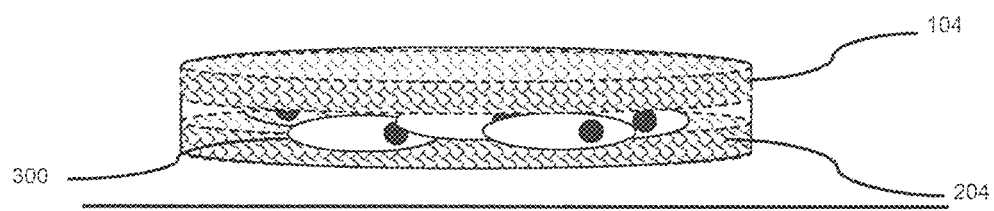
FIG. 8 is an isometric view of white adipose tissue sandwiched between two layers of supporting cells, according to an exemplary embodiment of the present disclosure.

In an exemplary embodiment, a first culture dish 200 having a layer of thermoresponsive material on the surface of a first culture dish base 201 may be used to culture a layer of supporting cells 204. Insert 100 may be placed through the opening 202 of the first culture dish 200 such that the surface 102 of the insert 100 may contact the layer of supporting cells 204. Conditions in the culture environment may be altered to activate the thermoresponsive material, e.g., change in temperature, and release the supporting cell layer 204 from the first culture dish 200 base surface 201, allowing adherence of the supporting cell layer 204 to the surface 102 of the insert 100. See, FIG. 4. Supporting cells 204 having been removed from a culture dish 200 base surface 201 by activation of a thermoresponsive material, and attached to the surface 102 of the insert 100 are also shown in FIG. 5.

In an exemplary embodiment, subcutaneous WAT samples may be procured from human subjects during elective surgical procedures. In this embodiment, sample sizes may range from about 100 to about 5000 grams of WAT tissue. In a particular embodiment, an experimental sample may be divided for various experimental purposes. In a particular embodiment, a portion of the subcutaneous WAT sample, e.g., 10 grams, may be minced, flash frozen, and stored as a matched primary WAT sample. In a particular embodiment, a portion of the subcutaneous WAT sample, e.g., 10 grams, may be stored in a nucleic acid lysis buffer, e.g., RNeasy Lipid Tissue Mini Kit™ (Qiagen), as a matched primary WAT sample for transcriptional confirmation. In particular embodiment, a portion of the subcutaneous WAT sample, e.g., 25 grams, may be used to produce SWAT cultures according to embodiments of the present disclosure. In a particular embodiment, a portion of the subcutaneous WAT sample, e.g., 25 grams, may be used to isolate matched supporting cells, e.g., adipocites ADSCs for differentiation into diffAds using a standard protocol when the WAT is minced, enzymatically digested, and centrifuged.

In an exemplary embodiment of the present disclosure, primary, human WAT may be isolated from a patient and mechanically minced into segments 300. WAT tissue segments 300 may be transferred to a culture dish 400 having a layer of supporting cells 304 growing on a culture dish base 401. See, FIG. 6.

Insert 100 having a layer of supporting cells 204 may then be inserted into culture dish 400 including WAT tissue 300 atop a layer of supporting cells 204. See, FIG. 7. In this embodiment, the primary, human WAT tissue 300 may then be sandwiched between two layers of supporting cells, 204, 304, to form a sandwich WAT (SWAT) co-culture system 800. See, FIG. 8. Upper supporting cell layer 104 may be attached to the base 102 of insert 100 and serve to hold the buoyant WAT tissue 300 in contact with the underlying layer of supporting cells 204 attached to culture dish 200 until adhesion occurs. In an exemplary embodiment, adhesion between the WAT tissue 300 and the layers of supporting cells 104, 204 occurs within minutes. In certain embodiments, the bi-layer construct of the SWAT system may be entirely cellular or may contain various synthetic or acellular components.

In an exemplary embodiment, 0.5-1 mm segments of human, primary WAT tissue are sandwiched between two layers of supporting cells, e.g., adipose-derived stromal cells (ADSCs), to form the SWAT co-culture system described herein. Supporting cells, e.g., ADSCs, may be cultured on standard tissue culture plates coated with a thermoresponsive substrate. The SWAT culture system as disclosed herein may also a standard culture media. Examples of standard culture media including at least low glucose DMEM, about 10% newborn calf serum, and about 1% penicillin/streptomycin antibiotic solution.

In exemplary embodiments, the SWAT system described herein may be utilized as a test model for any extrinsic factor or system intended to modify the biology or physiology of adipose tissue or adipocytes. In various embodiments, test factors may be introduced to the cell culture medium and their impact evaluated in the isolated human adipocytes or segments of primary, human WAT. Non-limiting embodiments of test factors may include but are not limited to pharmaceutical compounds, recombinant or native viruses, recombinant or isolated nucleic acid constructs, expression vectors, siRNA construction, micro RNA constructs, genetic tools, bacteria, and environmental modulations including temperature, pressure, and modulation of gases.

As illustrated in the micrographs of FIG. 9A, a SWAT culture is established between a bi-layer of supporting cells. The WAT is added to a bottom layer of unlabeled supporting cells and a top layer of supporting cells expressing enhanced green fluorescent protein (eGFP) is added. As shown in FIG. 9A, a WAT cluster of cells is sandwiched between a bi-layer of supporting cells, e.g., eGFP negative (bottom layer) and eGFP positive (top layer) to forming an exemplary SWAT culture system. Moreover, FIG. 9B shows microscopic images of a SWAT culture over time. The WAT cell clusters within SWAT culture are capable of retaining their morphologic stability for up to at least 47 days or about 6.7 weeks. See, FIG. 9B.

Figure 10:
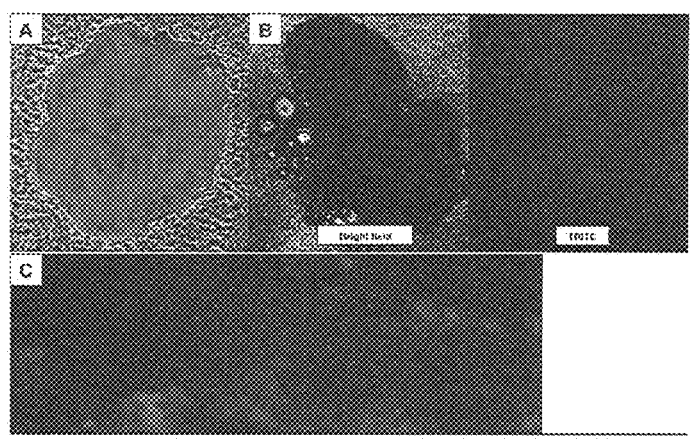
FIG. 10 is a series of microscopic images showing the long-term stability of a WAT cell cluster in a SWAT culture system, according to an exemplary embodiment of the present disclosure.

In various embodiments, the SWAT co-culture system described herein demonstrate long-term viability and stability which are important features for micro-physiologic models of terminally differentiated cells including WAT. In an exemplary embodiment of the present disclosure, long-term morphological stability is illustrated in staining of SWAT clusters in FIG. 10. Structural stability of the WAT cell clusters is demonstrated in FIG. 10A by restriction of neutral lipids to only WAT cells even after 51-days in SWAT culture. Likewise, propinium iodine staining of WAT cells in a SWAT culture was negative as seen in FIG. 10B. Propinium iodine negative WAT cells indicates that, after at least 18 days of SWAT culture, WAT cells were not undergoing programmed cell death, i.e., apoptosis. Finally, restriction of lipophilic staining to the adipocytes of the SWAT co-cultures further evidences the long-term viability of the systems and methods described herein. See, FIG. 10C. In contrast to conventional methods, an exemplary embodiment of the present disclosure demonstrates that the WAT cell clusters within SWAT cultures maintain their intracellular architecture, e.g., FIG. 10A, are viable and not entering a state of programmed cell death, e.g., FIG. 10B, and are maintained as separate populations.

Figure 11:
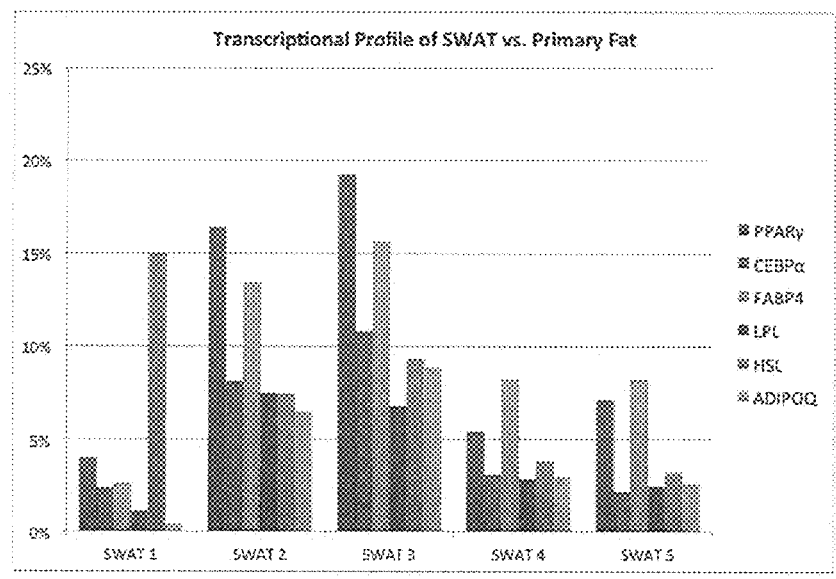
FIG. 11 is a graphical illustration showing that SWAT cultures are transcriptionally active and express genes associated with adipose tissue identity, according to an exemplary embodiment of the present disclosure.

FIG. 11 demonstrates that the SWAT system described herein is capable of maintaining a gene expression profile of at least six (6) key adipocyte identity genes including: activated receptor gamma (PPARγ), which is a master regulator of adipocyte differentiation/identity; fatty acid binding protein 4 (FABP4), which is a transcription factor necessary for terminal adipocyte differentiation; CCAAT/enhancer-binding protein alpha (CEBPα), which delivers long-chain fatty acids and retinoic acid to nuclear receptors; lipoprotein lipase (LPL), which is an enzyme that hydrolyses triglycerides; hormone sensitive lipase (HSL), which hydrolyzes stored triglycerides to free fatty acids; and adiponectin (ADIPOQ), which is a central adipokine in the control of fat metabolism and insulin sensitivity. Experimentally, total RNA was collected from SWAT cultures and expression levels were compared to subject-matched primary WAT using reverse transcription polymerase chain reaction (RT-PCR). At a transcriptional level, the SWAT culture system of the present disclosure maintains the adipose tissue identity. See, FIG. 11.

Figure 12:
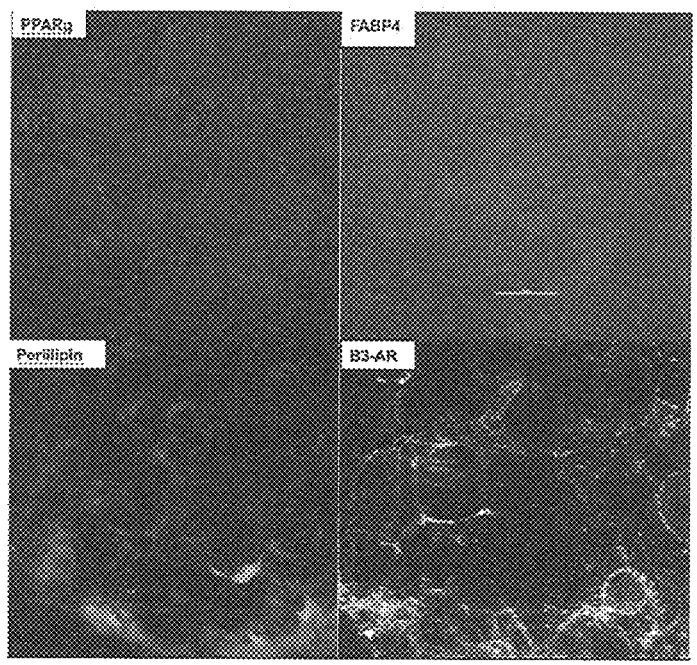
FIG. 12 shows microscopic images indicating that SWAT cultures are translationally active and express protein associated with adipose tissue identity, according to an exemplary embodiment of the present disclosure.

At a translational level, the SWAT culture system of the present disclosure also maintains adipocyte proteins. As seen in FIG. 12, immunocytochemistry staining of SWAT cultures demonstrates the protein production of adipocyte markers including: PPARg, FABP4, beta-3 adrenergic receptor (B3-AR), which is associated with lipolysis in adipocytes, and perillipin, which is also known as protein lipid droplet-associated protein and coats lipid droplets in adipocytes.

Figure 13A:
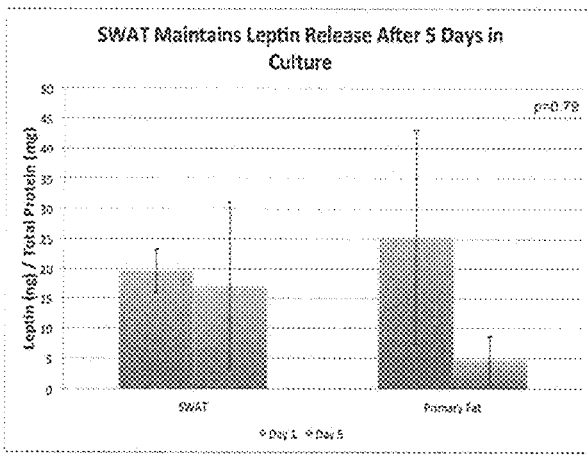
FIG. 13A is a graphical illustration showing that SWAT cultures secrete leptin at basal levels on days 1 and 5 of culture, which mirrors primary WAT, according to an exemplary embodiment of the present disclosure.
Figure 13B:
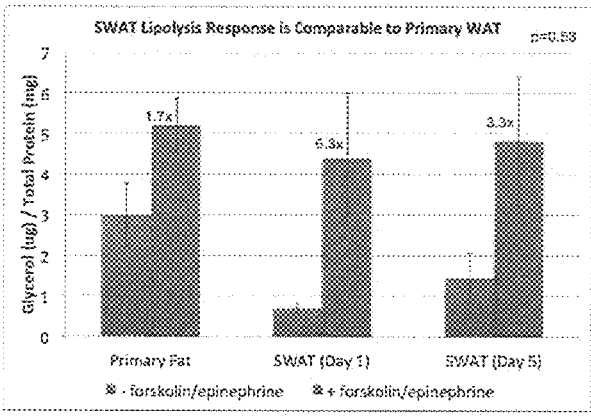
FIG. 13B is a graphical illustration showing that SWAT cultures secrete adiponectin at basal levels on days 1 and 5 of culture, which mirrors primary WAT, according to an exemplary embodiment of the present disclosure.

In addition to expressing gene and protein markers associated with adipocytes, SWAT cultures of the present disclosure also perform basal endocrine functions. In certain embodiments of the present disclosure, it may be desirable to maintain the functionality of tissues and cells in culture models as close the native tissue as possible. In various embodiments, SWAT clusters maintain their native endocrine function. Primary, human WAT is an endocrine tissue which secretes at least 2 hormones including: leptin and adiponectin. Based on normalized, quantitative ELISA assays, as illustrated in FIG. 13A and FIG. 13B, SWAT cultures secrete leptin and adiponectin at similar levels as subject-matched WAT after both one (1) and five (5) days in culture. See, FIG. 13A and FIG. 13B.

Figure 13C:
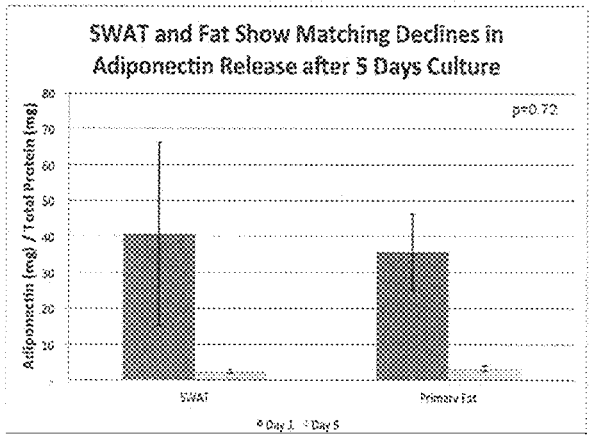
FIG. 13C is a graphical illustration showing that SWAT cultures perform lipolysis in response to catecholamine stimulation after days 1 and 5 in culture, according to an exemplary embodiment of the present disclosure.

Further, the SWAT culture system described herein performed lipolysis at levels similar to primary WAT in response to exogenous signals. See, FIG. 13C. Lipolysis, which is the process of converting stored fats into metabolic fuel, is a central function of WAT. In vivo, lipolysis occurs at a basal rate and is upregulated by catecholamines. In vitro, lipolysis can be quantified by measuring the amount of free glycerol released with normalization to total protein levels using a conventional Bradford total protein assay. In a particular embodiment of the present disclosure, SWAT cultures were exposed to 100 µM forskolin+1 µM epinephrine for three (3) hours. After 1-day and 5-days in culture, SWAT cultures performed lipolysis at levels similar to primary WAT in response to stimulation.

Figure 14:
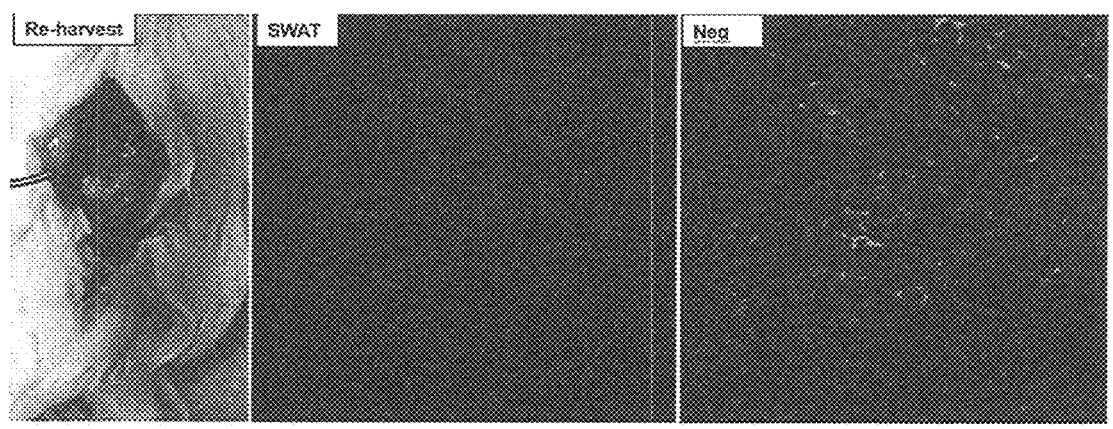
FIG. 14 shows images illustrating that SWAT cultures fully engraft into immunocompromised, eGFP-labeled mice, according to an exemplary embodiment of the present disclosure.

In another exemplary embodiment, the SWAT culture system described herein may maintain native functionality after at least ten days of SWAT culture. As shown in FIG. 14, a SWAT culture was harvested after ten days of SWAT culture and subcutaneously injected into immunocompromised eGFP-labeled mice (NOD-scid IL2Rγnull). It is known that implanted tissue must recruit a new blood supply, i.e., induce vascularization, or the tissue will die, i.e., necrosis, within 48 hours and subsequently be liquefied by the host. In an exemplary embodiment, SWAT transplants were re-harvested from their mice hosts ten days after subcutaneous injection. Upon visual examination, the injected SWAT tissues were readily seen by the naked eye. See, FIG. 14 (Re-harvest). Further, histological analysis revealed that the SWAT transplants retained the architecture characteristic of WAT, and did not express eGFP endogenous to the mouse host. See, FIG. 14 (SWAT and Neg). This data indicates that SWAT cultures may retain sufficient native functionality to enable SWAT tissue engraftment even after ten days in SWAT culture. Because recruitment of new, host blood supply, i.e. vascularization, is a highly complex process, this data further indicates that the SWAT system described herein may be a robust, micro-physiologic model of human WAT.

Exemplary embodiments of the present disclosure provide a system that may allow investigation into effective anti-obesity strategies. It was previously understood that only brown adipose tissue (BAT) was capable of burning energy in a process known as thermogenesis. However, in both rodents and diffAds models, it is known that white adipocytes (wAds) could be induced to become thermogenic beige/"brite" adipocytes (brAds), which may be identified biochemically based on an upregulation of uncoupling protein 1 (UCP1) in response to elevated intracellular cyclic AMP (cAMP) levels. Specifically, induction of UCP1 transforms WAT into thermogenic cells and leads to an alternation in the cellular morphology.

Morphologically, brAds shift from a large, unilocular phenotype associated with WAT cells to a multilocular phenotype. The WAT-specific source of brAds has been confirmed by lineage tracing studies in rodents: brAds are myogenic factor 5 (Myf5) negative whereas brown adipocytes (bAds) share a Myf5+ lineage with skeletal myocytes. In rodents, browning has been observed in most subcutaneous and visceral WAT depots. In rodent models, the weight-loss incurred by browned WAT can be profound. Accordingly, the SWAT culture system as disclosed herein may provide a micro-physiological model system for evaluating controlled browning of culturing primary, human WAT as a feasible and effective anti-obesity strategy.

Embodiments of the present disclosure provide systems and methods for investigating the biochemistry of browning pathways identified in rodent and diffAds models which may be controlled by: beta-3 adrenoreceptors (ß3-ARs), cold receptors, cardiac natriuretic receptors, Janus inhibitor kinase 3 (JAK3), and Notch 1. Each of these endogenous biochemical pathways provide numerous candidate targets for pharmaceutical intervention. Several compounds have browned WAT in rodents and in diffAds. In rodents, chemical induction of browned WAT successfully ameliorated obesity and cured type 2 diabetes. Accordingly, the SWAT culture system as disclosed herein may provide a micro-physiological model system for evaluating candidate pharmaceuticals in primary, human WAT tissues.

Exemplary embodiments of the present disclosure provide an in vitro system that may allow investigation and evaluation into the effects of chemical compounds, such as pharmaceuticals, on human WAT and other buoyant cell types. Non-limiting, exemplary candidate pharmaceuticals may include but are not limited to: agonists and antagonists of beta-3 adrenoreceptors, e.g., 1&3-ARs; migrabegron, which is a 4th generation 1&3 agonist FDA-approved for use in overactive bladder syndrome, but is known to activates BAT in humans; CL-316243, which is a specific 1&3 agonist, e.g., 1&1, 1&2, 1&3=0:1:100,000) that ameliorated obesity in obese, diabetic yellow KK mice; L-796568, which is a benzenesulfonamide-family specific 1&3 agonist, e.g., 1&1, 1&2, 1&3=1:230:660, that improved energy expenditure but did not generate notable anti-obesity effects in obese human males; BRL 26830A, which is a 1&3 agonist that demonstrated significant improvements in weight loss in a double-blinded trial.

In other exemplary embodiments, the culture system described herein may maintain native functionality of other buoyant cells in culture. Endogenous biochemical pathways may be evaluated for pharmaceutical intervention by applying and evaluating the impact of exogenous stimuli, e.g., chemical compounds. Any buoyant cell type, regardless of tissue type or species of origin, may be a candidate for use in embodiments of the present disclosure. Exemplary embodiments of buoyant tissues and cell types that may be candidates for evaluation using the apparatuses, systems and methods disclosed herein include but are not limited to: hepatocytes, renal tissue and cells, brain tissue and cells, thyroid tissue and cells, splenic tissue and cells, liver tissue and cells, central and peripheral nervous tissue and cells, and immunologic tissue and cells. Moreover, buoyant cells may be obtained from any source organism. Exemplary source organisms may include but are not limited to: plants, animals, protists, fungi, archaebacteria, and eubacteria. Additional exemplary sources of tissue or cells for evaluation using the apparatuses, systems and methods disclosed herein include but are not limited to: human, mouse, rat, monkey, dog, cat, pig, non-human primates, and fish.

Exemplary embodiments of the present disclosure provide systems and methods for investigating the biological responses of exemplary, non-limiting cell types. For example, an established buoyant tissue type may include neuronal tissue. Neuronal tissue may not readily adhere to the surface of culture dishes if, for example, excessive bubbles are introduced to an aqueous culture media. Accordingly, the buoyant tissue culture apparatuses, systems and methods disclosed herein may be directly applied to the study of neuronal tissue.

Embodiments of the present disclosure provide apparatuses, systems and methods for culturing neuronal tissue which may include embryonic or adult neuronal tissues. In an exemplary embodiment, the present disclosure provides a model system which may be used in the evaluation of neurogenesis. In other embodiments, the present disclosure may provide a system in which neuronal disease progress may be evaluated.

In an exemplary embodiment, the apparatuses, systems and methods of the present disclosure may be used to evaluate the biochemical pathways leading to the neuronal disease commonly known as Alzheimer's Disease (AD) and as well as the impact of various pharmaceutical interventions. For example, central to AD disease is the differential processing of the integral membrane protein Amyloid Precursor Protein (APP) in the normal versus disease state. In the normal state, APP is initially cleaved by α-secretase to generate sAPP and a C83 carboxy-terminal fragment. The presence of sAPP is associated with normal synaptic signaling and results in synaptic plasticity, learning and memory, emotional behaviors, and neuronal survival. In the disease state, APP is cleaved sequentially by α-secretase and γ-secretase to release an extracellular fragment called A 40/42. This neurotoxic fragment frequently aggregates and results in A 40/42 oligomerization and plaque formation. A 40/42 aggregation results in blocked ion channels, disruption of calcium homeostasis, mitochondrial oxidative stress, impaired energy metabolism and abnormal glucose regulation, and ultimately neuronal cell death. The micro-physiological system of the present disclosure provides a model for quickly and efficiently assessing buoyant neuronal tissues in vitro while maintaining the neuronal tissue in a native state.

Embodiments of the present disclosure provide apparatuses, systems and methods for evaluating the biochemical pathways involved in cardiovascular disease (CVD). Cardiovascular disease (CVD) remains the leading cause of death in the United States, with over 600,000 deaths per year and annual direct costs near $300 billion. High blood pressure (HTN) and obesity are two of the most prevalent and modifiable risk factors for CVD. HTN affects 29.1% of adult Americans and successfully treating blood pressure decreases CVD risk by 20-50%. Obesity is more prevalent than HTN, affects 36% of adult Americans and is considered a global epidemic. However, while several classes of anti-hypertensive medications are available, no broadly effective anti-obesity medications have been approved for patient use.

In an exemplary embodiment, the apparatuses, systems and methods of the present disclosure may be used to evaluate the overlapping biochemical pathways involved in cardiovascular disease and obesity. For example, the pathogenesis of HTN often involves over-activation of the renin-angiotensin system (RAS). RAS over-activation has also been linked to obesity, a disease involving the overgrowth of WAT. Moreover, the RAS shares biochemical signaling pathways which overlap with obesity biochemical pathways as evidenced by the fact that: (i) the molecular components of RAS are present in adipose tissue, (ii) WAT secretes angiotensinogen (AGT), (iii) angiotensin II (Ang II) may induce adipogenesis in isolated adipocytes and differentiated adipocytes (diffAds), (iv) Ang II stimulation inhibited lipolysis in ex vivo human adipocytes, thus favoring adipogenesis.

Moreover, embodiments of the present disclosure confirmed that SWAT cultures are capable of maintaining RAS pathway constituent expression. For example, using RT-PCR it was determined that SWAT cultures preserves expression of key RAS components (n=5): (i) SWAT AGT expression: 62% of primary WAT (range 47-79%); SWAT ACE expression: 58% of primary WAT (range 45-71%), SWAT AT1R expression: 14% of primary; WAT (range 6-19%); SWAT AT2R expression: 231% of primary WAT (range 72-617%), SWAT Renin: no detectable expression. Further, in terms of endocrine function, SWAT secretes AGT, leptin and adiponectin as determined via enzyme-linked immunosorbent assays (ELISA). Finally, SWAT secretes 77 to 204 ng AGT per mg of total protein, and ELISA testing identified no Ang II in media from cultured SWAT. Together, this data indicates that RAS over-activation may drive adipogenesis in both systemic and autocrine fashion. In embodiments, RAS inhibition through current, approved pharmacotherapies may ameliorate both hypertension and obesity. Embodiments of the present disclosure provide apparatuses, systems, and methods for investigation into this system.

While the embodiments are described with reference to various implementations and exploitations, it will be understood that these embodiments are illustrative and that the scope of the inventions is not limited to them. Many variations, modifications, additions, and improvements are possible. Further still, any steps described herein may be carried out in any desired order, and any desired steps may be added or deleted.

The invention claimed is:

1. A micro-physiological system, comprising:
   a culture comprising an aqueous culture medium and a buoyant tissue sandwiched between two layers of supporting cells, wherein the buoyant tissue is buoyant relative to the aqueous culture medium and the buoyant tissue comprises primary, human white adipose tissue (WAT);
   an exogenous agent configured to be added to the culture; and
   at least one detector configured to evaluate a physiological change in the WAT as a result of adding the exogenous agent to the culture.

2. The system of claim 1, wherein the culture is operable to maintain the sandwiched WAT in a viable, differentiated state for at least three days.

3. The system of claim 1, wherein the exogenous agent comprises at least one of a chemical, a pharmaceutical, a nucleic acid, a protein, a virus, a lipid, and a vector.

4. The system of claim 1, wherein the detector comprises at least one of an optical detector, a biochemical detector, and an energy detector.

5. The system of claim 1, wherein the physiological change comprises at least one of an intracellular change, an extracellular change, a transcriptional change, a translational change, a post-transcriptional change, a post-translational change, a secretion change, and a functional change.

6. The system of claim 1, wherein said micro-physiological system comprises an organ-on-a-chip system.

7. The system of claim 1, wherein the WAT and the two layers of supporting cells are submerged in the aqueous culture medium.

8. The system of claim 1, wherein the buoyant tissue comprises an organ.

9. The system of claim 1, wherein the buoyant tissue comprises a tissue explant.

10. The system of claim 1, wherein the buoyant tissue comprises a 0.5-1 mm segment of tissue sandwiched between the two layers of supporting cells.

11. The system of claim 1, wherein the exogenous agent comprises a candidate pharmaceutical, and
    wherein the system is operative to evaluate the candidate pharmaceutical in the WAT.

12. The system of claim 1, wherein the physiological change comprises browning of the WAT.

13. The system of claim 1, wherein the culture is operable to maintain the sandwiched WAT in a viable, terminally differentiated state for at least one day.

14. The system of claim 1, wherein the culture is operable to maintain the sandwiched WAT in a viable, terminally differentiated state for at least five days.

15. The system of claim 1, wherein the culture is operable to maintain the sandwiched WAT in a viable, terminally differentiated state for at least ten days.

* * * * *